United States Patent [19]

Fontirroche et al.

[11] Patent Number: 5,063,018

[45] Date of Patent: Nov. 5, 1991

[54] EXTRUSION METHOD

[75] Inventors: Carlos A. Fontirroche, Coral Gables; Csaba Truckai, Miami, both of Fla.

[73] Assignee: Cordis Corporation, Miami Lakes, Fla.

[21] Appl. No.: 532,626

[22] Filed: Jun. 4, 1990

[51] Int. Cl.$^5$ ............................................. B29C 47/20
[52] U.S. Cl. ............................ 264/514; 156/244.13; 156/244.15; 264/173; 264/174; 264/209.8; 425/133.1; 425/380; 425/403; 425/467
[58] Field of Search ................... 264/209.8, 149, 209.3, 264/209.1, 150, 209.7, 563, 173, 174, 209.4, 514, 516; 425/380, 133.1, 467, 466, 403; 156/244.13, 244.15

[56] References Cited

U.S. PATENT DOCUMENTS

| | | | |
|---|---|---|---|
| 3,755,525 | 8/1973 | Sheridan et al. | 264/209.3 |
| 3,792,951 | 2/1974 | Meyers | 425/380 |
| 4,100,246 | 7/1978 | Frisch | 264/150 |
| 4,277,432 | 7/1981 | Woinowski | 264/209.8 |
| 4,321,226 | 3/1982 | Markling | 264/149 |
| 4,636,346 | 1/1987 | Gold et al. | 264/149 |
| 4,655,987 | 4/1987 | Zertuche | 264/563 |
| 4,753,765 | 6/1988 | Pande | 264/149 |
| 4,764,324 | 8/1988 | Burnham | 264/150 |
| 4,904,431 | 2/1990 | O'Maleki | 264/149 |

FOREIGN PATENT DOCUMENTS 2395915  3/1979  France ............................ 264/209.3

Primary Examiner—Jeffery Thurlow
Attorney, Agent, or Firm—Gerstman & Ellis, Ltd.

[57] ABSTRACT

Multiple lumen tubing is extruded by first extruding an inner tube of molten plastic about a metallic, bore-forming mandrel wire, followed by extruding about the inner tube an outer tube of molten plastic having a lumen formed by air mandrel means, with the inner and outer tubes being bonded together. This may be accomplished by means of a mandrel which is positioned in an extrusion die, with the mandrel defining a distal end portion positioned and shaped to form a lumen in the tubing, and an air flow passage extending through the mandrel to provide an air mandrel to the newly formed lumen to prevent its collapse. The distal end portion of the mandrel may be carried by an intermediate neck portion which has at least one transverse dimension that is less than the corresponding transverse dimension of the distal end portion.

23 Claims, 1 Drawing Sheet

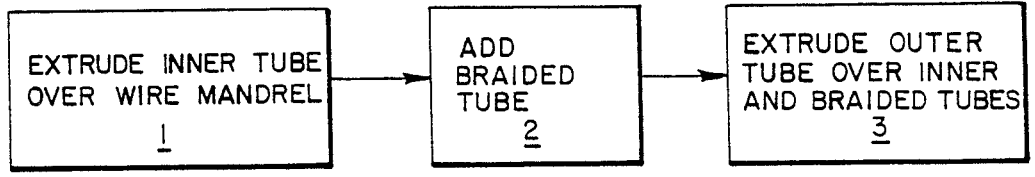
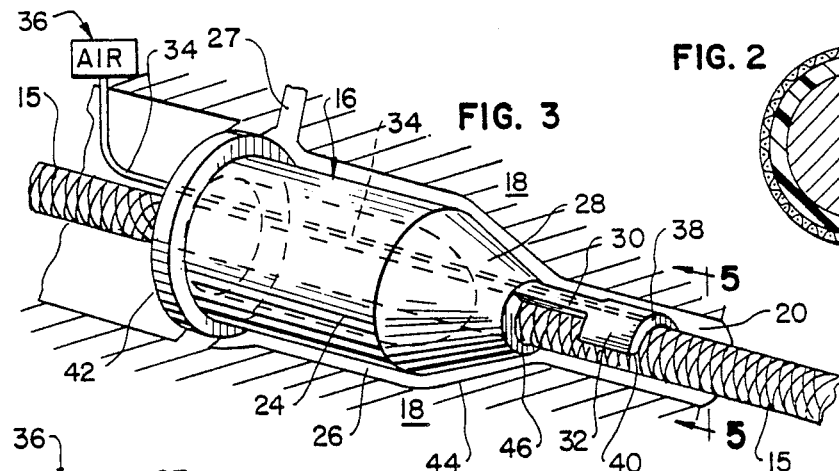
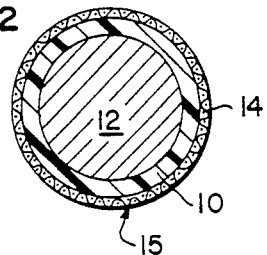
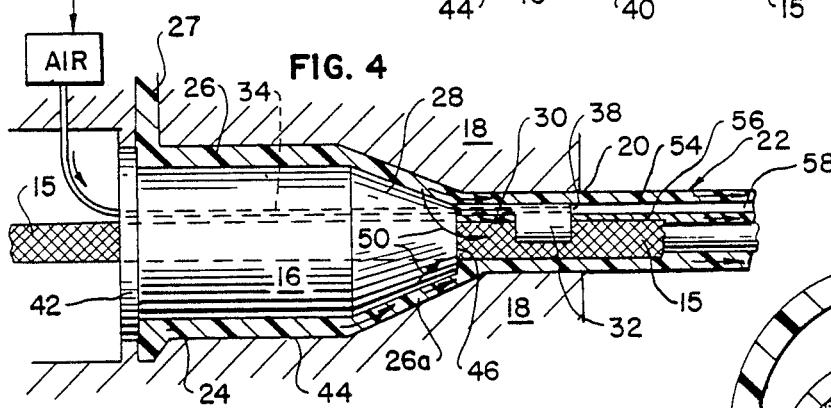
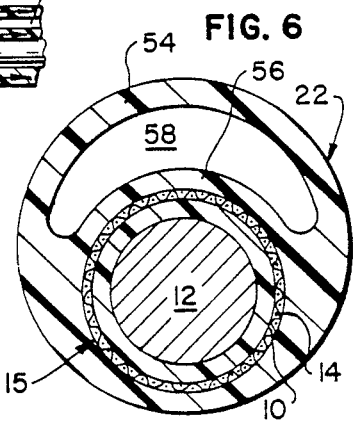
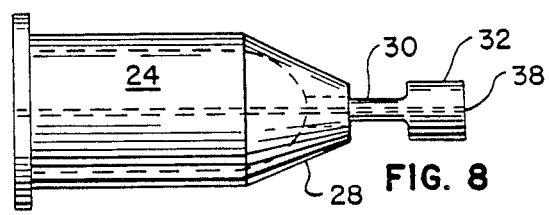
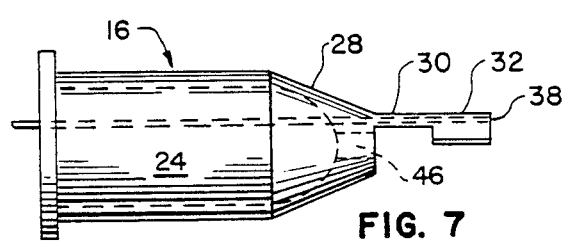
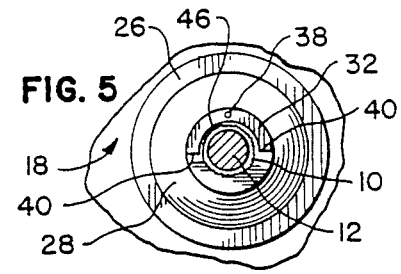

EXTRUSION METHOD

BACKGROUND OF THE INVENTION

In the manufacture of small catheters, sometimes two or more lumens are needed that extend within the catheter. This has been previously accomplished by extrusion of the catheter about a plurality of metal mandrels, which then must be removed after the extrusion process to open the lumens. Typically, the metal mandrels are made of a copper alloy which can be stretched to facilitate their removal. However, the mandrel is then typically no longer useful, so that it must be recycled by melting and reextruded as a new mandrel.

Thus, there is a perceived need to reduce the number of expensive metallic mandrels which are used in the extrusion of catheters and the like.

Additionally, air mandrels have been used, in which the lumen of an extruded tube is maintained after its formation by means of a gentle air pressure. However, it has proven most difficult to manufacture multiple lumen catheters or the like with the use of air mandrels.

By this invention, a combined extrusion process is provided which exhibits advantages found in both air mandrel extrusion and wire mandrel extrusion. Specifically, a good bond can be obtained between various layers of catheters extruded by this invention. Also, great versatility is provided in the specific shape of at least one of the lumens provided in the extrusion process of this invention. For example, a lumen of crescent-shaped cross-section can be provided without the need for the use of a correspondingly-shaped wire mandrel which, of course, would add to the expense of the catheter. Nevertheless, advantages of good layer bonding and the like which are characteristic of wire mandrel catheter extrusion processes can be achieved in this invention.

DESCRIPTION OF THE INVENTION

This invention relates to an extrusion process for the manufacture of multiple lumen tubing, which comprises a first step of extruding an inner tube of molten plastic about metallic, bore-forming mandrel means. More than one mandrel may be provided at this point if more than two bores or lumens are desired in the resulting tubing, which tubing is typically used as a catheter.

Then, one may optionally apply a tubular supporting member of crossing strands, preferably braided strands, to the outer surface of the inner tube to form a coaxial structure of the inner tube and tubular supporting member.

Following this, one may extrude about the inner tube (and the optional tubular supporting member on the outer surface thereof) an outer tube of molten plastic having a lumen formed by air mandrel means. In this process, sufficient pressure may be applied by means of a die of the design as shown herein so that the inner and outer tube have attached wall portions. Typically, the inner and outer tubes become bonded to the crossing-strand tubular supporting member if it is present, to achieve such attached wall portions. Additionally, the inner and outer tubes may be directly bonded to themselves, either in the absence of such a tubular supporting member, or by the migration of molten plastic material in the second extrusion step inwardly through the tubular supporting member to cause bonding of both tubes to each other.

Preferably, the inner and outer tubes that result from the extrusion process of this invention are eccentrically positioned, in that their central axes are spaced from each other, although the inner tube is typically entirely surrounded by the outer tube. Also, the outer tube typically defines an eccentric lumen, being spaced from the axis of the outer tube. This eccentric lumen may be of a large variety of desired cross-sectional shapes, depending on the shape of the particular extrusion die. Particularly, the eccentric lumen may be generally crescent-shaped.

The metallic mandrel means of the first extrusion step described above is preferably present and occupying the portion of the inner tube about which the outer tube is extruded during that extrusion process. This permits higher pressure extrusion to take place and better bonding.

Preferably, the air pressure of the air mandrel means over ambient pressure is about the pressure of two to eight inches of water, during the second extrusion step described above.

The above process is preferably accomplished with an extrusion die which includes a mandrel for extrusion of tubing while the mandrel is positioned in an extrusion die that defines the outer diameter of tubing extruded through the die. As is conventional, the extrusion mandrel may define an extrusion head for positioning within the die. The head may define a distal end portion which is positioned and shaped to form a lumen in tubing extruded through the die. An air flow passage is provided, extending through the mandrel to communicate with the lumen formed in the extruded tube for providing the above-described air mandrel means. Such air mandrel means prevents the collapse of the lumen that would otherwise take place immediately after extrusion, by providing a typically-gentle pressure within the freshly extruded lumen.

In accordance with this invention, the distal end portion of the mandrel is carried by an intermediate neck portion thereof. The neck portion has at least one transverse dimension, and preferably both transverse dimensions, which are less than the corresponding transverse dimensions of the distal end portion. Thus, room is provided in the area adjacent the intermediate neck portion for molten plastic material to distribute, to penetrate about all transverse sides of the distal end portion: above, below, and to the sides thereof, to facilitate the formation of the extruded tubing about the lumen-defining distal end portion within the extrusion die. This neck portion of the mandrel makes possible the use of distal end portions having irregular cross-sectional shapes, for the formation of lumens in extruded tubing of any of a wide variety of desired cross-sectional shapes other than circular, although this invention may also be used to form an air-inflated lumen of cylindrical shape as well. For example, a crescent-shaped lumen is formed in the specific embodiment of this invention, with the distal end portion of the mandrel also being correspondingly crescent shaped but with squared-off ends.

Additionally, the mandrel of this invention defines an aperture which is proximally positioned to the distal end and neck portions of the mandrel. This aperture is used to provide through the aperture inner, preformed tubing to the extrusion site defined at the distal end portion, when the same is positioned within an extrusion die. Thus, the mandrel serves to permit application by extrusion of an outer tubing about preformed, inner tubing, which optionally carries the crossing-strand tubular supporting member, in a process such as that described above.

DESCRIPTION OF DRAWINGS

In the drawings,

FIG. 1 is a diagram of the steps of the method of this invention;

FIG. 2 is a transverse, cross-sectional view of tubing as produced by an intermediate step of the method of FIG. 1;

FIG. 3 is a fragmentary, perspective view of an extrusion die and mandrel in accordance with this invention for practicing the third step of the method as described in FIG. 1;

FIG. 4 is a longitudinal sectional view of the structure of FIG. 3 showing molten plastic compound for extrusion being applied, taken along line 5—5 of FIG. 3;

FIG. 5 is an elevational view showing the distal end of the mandrel of FIG. 3;

FIG. 6 is an enlarged, transverse sectional view of the extruded tubing after manufacture by the method of this invention, prior to removal of the wire mandrel by conventional means;

FIG. 7 is an elevational view of the mandrel of FIGS. 3 and 4; and

FIG. 8 is a plan view of the mandrel of FIGS. 3 and 4.

DESCRIPTION OF SPECIFIC EMBODIMENTS

Referring to FIG. 1, the steps of the extrusion method of this invention are broadly outlined. As stated, Step 1 is a generally conventional step of extruding inner tube 10 over wire mandrel 12, as illustrated in FIG. 2. This process, which is per se conventional, results in a tube having a cylindrical bore after the wire mandrel is removed. Such mandrel is conventionally made of a silver-coated copper alloy, which is stretched after the extruded tubing is cool, and after the tubing has been cut to desired lengths for catheters or the like. Upon such stretching, the wire mandrel reduces its diameter, and does not snap back as does a typical tubing made of an elastomer such as polyurethane or the like. Thus, when the tubing snaps back to its original position, the mandrel breaks loose from its contact with the lumen of the tubing and can be removed.

Following this, Step 2 may be applied where desired: the addition of conventional, braided wire strand tubing 14 or the like. Alternatively, a tubular array of crossing strands which are not braided may be used, if desired. For such application, catheter 10 may be once again stretched to reduce its outer diameter, and then released again when the braided tubing 14 has been applied, so that the outer surface of catheter tubing 10 is in good contact with braided wire tubing 14. Additionally, braided wire tubing 14 may be solvent sealed or heat sealed into bonded relationship with the inner catheter 10, to form tubing 15.

Following Step 2, Step 3 takes place in which an outer tube is extruded over the inner tube 10 and the optional braided tube 14 which may be present. This extrusion step is illustrated by the remaining FIGS. 3-8, with the resulting product being shown in FIG. 6.

Extrusion mandrel 16 is shown in FIGS. 3 and 4 to reside in the bore of an extrusion die 18, which is shown in diagrammatic manner since die 18 may be of conventional configuration. Die 18 defines an extrusion orifice 20, which defines the outer diameter of the final tubing product 22.

Mandrel 16 resides within die 18, as shown. The proximal portion 24 of mandrel 16 defines, with die 18, an annular space 26 which communicates at its proximal end with one or more inlet ports 27 for providing a source of molten plastic material for extrusion.

Mandrel 16 also defines a frustoconical portion 28 which tapers down to a neck portion 30, which connects at one end to frustoconical portion 28 and at the other end to head which comprises distal end portion 32.

Conduit 34 communicates through mandrel 16 proximally to an air supply 36, with conduit 34 extending distally to a front aperture 38 defined in distal end portion 32.

Distal end portion 32 can be seen, particularly in FIGS. 3 and 5, to be of a crescent shape, but with ends 40 that are squared off. As shown, distal end portion 32 is larger in both of its transverse dimensions than neck portion 30, this enlargement being specifically shown in each of the transverse dimensions respectively by FIGS. 7 and 8.

Thus, mandrel 16 can be positioned within extrusion die 18 as shown, with flange 42 of the mandrel holding it in position with respect to die 18 in any conventional manner, so that most of the active mandrel portions are spaced from the inner, flow channel defining walls 44 of die 18. Thus, molten plastic for extrusion can enter through one or more sprue conduits 28 into the annular channel 26 defined between die 18 and mandrel 16. As particularly shown in FIG. 4, annular channel 26 tapers inwardly in a frustoconical shape at area 26a. Then, the frustoconical portion terminates, while molding compound flows in a distal manner into the area defined between die 18 and neck portion 30.

At the same time, the tubing 15, preformed in Steps and 2 of the method as described above, is advanced through the system defined by die 18 and mandrel 16, passing through hollow mandrel 16 and out of aperture 46 as defined at the distal end of frustoconical portion 28 of the mandrel. Thus, as shown particularly in FIG. 4, molten flowing plastic for extrusion enters the constricted, annular area distal to area 26a, as indicated by flow arrows 50. Because of the reduced transverse dimensions of neck portion 30, the flowing, molten plastic can easily migrate to fill the area between distal end portion 32 and frustoconical portion 28, at which point a significant pressure can build in the molten plastic, so that the molten plastic can migrate into the interstices of tubular member 14 made of crossing strands and/or can enter into intimate, bonding relation with the inner tube 10.

Also, molten plastic advances in a distal direction to be shaped into tube 22, with its outer diameter being constrained by the extrusion orifice 20 of die 18. The molten plastic material migrates all around the crescent-shaped distal end portion 32, to form outer wall portion 54 by extrusion between the top of distal portion 32 and die 18, as well as inner wall portion 56, which is formed by extrusion through a space 46 between distal portion 32 and inner tubular member 15.

Accordingly, as extrusion die 18 defines the outer diameter of extruded tubing 22, and as extruded tubing 22 completely surrounds the inner tubular member 15 that is fed to the extruder through mandrel 16, the generally crescent-shaped distal end portion 32 of the mandrel defines a second lumen 58 in the newly formed tubing 22. This newly formed lumen 58 is prevented from collapsing by the injection of air through air aperture port 38, typically at a pressure of about 3½ inches of water, which prevents the collapse of second lumen 58 as the extruded tubing 22 hardens. It can be seen that the resulting shape of second lumen 58 is not exactly the shape of distal portion 32 in that, particularly, the square ends 40 of distal portion 32 have rounded off a bit in the resulting lumen. By proper design of the distal mandrel portion 32, it is possible to form lumens 58 of a wide variety of desired shapes.

Typically, a polyurethane plastic may be used to form extruded tube 10 in the initial process, specifically Ducor brand polyurethane elastomer. Similarly, the plastic used to extrude tubing 22 over inner tubular member 15 ma be the same polyurethane elastomer, or any similar, preferably elastomeric, material. Such a polyurethane plastic may be melted to a temperature of about 348 degrees F. for optimal extrusion under conventional conditions. For example, the outer diameter of extruded tubing 22 may be 0.125 inch, with outer tubing 22 being extruded over the inner tubing member 15 with a barrel pressure for the molten plastic of about 2,000 p.s.i., for pressurization of the annular channel 26 and the like. A Killion extruder may be used with a KB-1 cross head. The screw may operate at 30 r.p.m., while the puller, which assists in advancement of the extruded tubing, may operate at 38 feet per minute.

The molten plastic used herein may be dried at 75 degrees C. under vacuum for 17 hours before melting and extrusion thereof to remove moisture from it.

The above described conditions are merely one preferred set of conditions. The invention of this application may be practiced under a variety of conditions which depend upon the plastic used, the dimensions of the product, and numerous other factors in a manner which is well understood by those skilled in the art.

After extrusion of tubing 22, it is cut to the desired lengths, typically the desired length of the catheter into which the tubing is to be made. The tubing is then typically stretched in a manner to stretch mandrel wire 12 along with it, causing the mandrel wire to achieve a reduced diameter. Then, when the elastomeric tubing 22, with its inner tubing 15, is released from tension, it snaps back, while the mandrel wire 12 does not snap back to an appreciable degree. The mandrel wire 12 can then be easily removed to provide an open first lumen in the catheter originally occupied by mandrel wire 12.

Thus, by the invention of this application, a multiple lumen catheter can be manufactured in which at least one of the lumens may be of a desired, non-circular cross sectional shape. This can be accomplished without the need for a second wire mandrel of non-circular cross-section, but at the same time good bonding can be achieved between inner tube 10 and outer tube 22, either with or without the presence of tubular supporting member 14. The resulting catheters in accordance with this invention may be manufactured with less expense and with greater reliability than the prior art analogs.

The above has been offered for illustrative purposes only, and is not intended to limit the scope of the invention of this application, which is as defined in the claims below.

That which is claimed is:

1. An extrusion process for the manufacture of multiple lumen tubing, which comprises:
   extruding an inner tube of molten plastic about metallic, bore-forming mandrel means; and
   extruding about said inner tube an outer tube of molten plastic having a lumen formed by air mandrel means, with said inner and outer tubes being attached with the axis of said outer tube being parallel to but spaced from the axis of said inner tube.

2. The process of claim 1 in which a tubular supporting member of crossing strands is added to said inner tube to form a coaxial structure of said inner tube and tubular supporting member, said outer tube being extruded about both said inner tube and said tubular supporting member.

3. The process of claim 1 in which said metallic mandrel means occupies the portions of said inner tube about which the outer tube is extruded as said extrusion takes place.

4. The process of claim 1 in which the air pressure of said air mandrel means over ambient pressure is from 2 to 8 inches of water during said extrusion.

5. The process of claim 1 in which said molten plastic is polyurethane.

6. The process of claim 1 in which said outer tube defines an eccentric lumen formed by said air mandrel means, said eccentric lumen being of non-circular cross section.

7. An extrusion process for the manufacture of multiple lumen tubing, which comprises:
   extruding an inner tube of molten plastic about metallic, bore-forming mandrel means;
   adding to said inner tube a tubular supporting member of crossing strands to form a coaxial structure of said inner tube surrounded by said tubular supporting member;
   and extruding about said inner tube and tubular supporting member of crossing strands an outer tube of molten plastic having a lumen formed by air mandrel means so that said inner and outer tubes are eccentrically positioned relatively to each other, said inner and outer tubes being bonded to each other, with the outer tube at least substantially surrounding said inner tube and tubular supporting member.

8. The process of claim 7 in which said metallic mandrel means occupies the portion of said inner tube about which the outer tube is extruded as said extrusion takes place.

9. The process of claim 8 in which the air pressure of said air mandrel means over ambient pressure is from 2 to 8 inches of water during extrusion.

10. The process of claim 8 in which said outer tube lumen formed by said air mandrel means is of non-circular cross section.

11. The process of claim 10 in which said molten plastic is polyurethane.

12. In a mandrel for extrusion of tubing while the mandrel is positioned in an extrusion die that defines the outer diameter of tubing extruded through said die, said mandrel defining an extrusion head for positioning within said die, said head defining a distal end portion positioned and shaped to form a lumen in tubing extruded through said die, and an air flow passage extending through said mandrel to communicate with the lumen formed in said extruded tube for providing air mandrel means, the improvement comprising, in combination:
   said distal end portion being carried by an intermediate neck portion of said mandrel, said neck portion having at least one transverse dimension that is less than the corresponding transverse dimension of said distal end portion, said distal end portion defining a transverse shoulder at its connection to the neck portion.

13. The mandrel of claim 12 in which both transverse dimensions of said neck portion are less than the corresponding dimensions of said distal end portion.

14. The mandrel of claim 12 in which said distal end portion has a cross-section that is generally crescent-shaped.

15. The mandrel of claim 12 which also defines an aperture which is positioned axially and proximally to said distal end portion, to provide inner, preformed tubing to the extrusion site defined at said distal end portion, for application by extrusion of outer tubing about said inner tubing.

16. The mandrel of claim 12, in combination with an extrusion die that defines the outer diameter of said extruded tubing.

17. In a mandrel for extrusion of tubing while the mandrel is positioned in an extrusion die that defines the outer diameter of tubing extruded through said die, said mandrel defining an extrusion head for positioning within said die, said head defining a distal end portion positioned and shaped to form a lumen in tubing extruded through said die, and an air flow passage extending through said mandrel to communicate with the lumen formed in said extruded tube for providing air mandrel means, the improvement comprising, in combination:

said distal end portion being carried by an intermediate neck portion of said mandrel, said neck portion being of less width in both transverse dimensions than the corresponding dimensions of said distal end portion, said mandrel also defining an aperture which is proximally positioned to said distal end portion, to provide inner, preformed tubing through said aperture to the extrusion site defined at said distal end portion, for application by extrusion of outer tubing about said inner tubing.

18. The mandrel of claim 17, in combination with an extrusion die that defines the outer diameter of said extruded tubing.

19. The mandrel of claim 18 in which said distal end portion has a cross-section that is generally crescent shaped.

20. The mandrel of claim 17 in which said distal end portion defines a transverse shoulder at its connection to the neck portion.

21. The mandrel of claim 20 in which said proximally positioned aperture is positioned to provide inner, preformed tubing through said aperture to the extrusion site in a position so that the axis of the inner tubing is parallel to but spaced from the axis of the outer tubing which is extruded about said mandrel and said inner tubing.

22. The mandrel of claim 21 in which said distal end portion has a cross section that is other than circular.

23. The mandrel of claim 12 in which said distal end portion is of non-circular cross section.

* * * * *